United States Patent [19]

Davis

[11] Patent Number: 5,302,982
[45] Date of Patent: Apr. 12, 1994

[54] PROJECTOR SLIDE APPARATUS

[75] Inventor: Deanne I. Davis, Hoffman Estates, Ill.

[73] Assignee: Woodlyn Inc., Arlington Heights, Ill.

[21] Appl. No.: 21,050

[22] Filed: Feb. 23, 1993

[51] Int. Cl.⁵ .............................................. A61B 3/02
[52] U.S. Cl. .................................. 353/30; 353/108; 351/239; 351/243; 351/233
[58] Field of Search ............... 353/120, 108, 109, 110, 353/84, 103, 97, 95, 30, 32; 351/213, 214, 233-235, 237, 239, 243, 244, 246

[56] References Cited

U.S. PATENT DOCUMENTS

| | | | |
|---|---|---|---|
| 1,949,067 | 2/1934 | Wheelock et al. | 351/237 |
| 3,294,472 | 12/1966 | Haugen | 351/237 |
| 3,294,473 | 12/1966 | Haugen | 351/237 |
| 3,341,275 | 9/1967 | Haugen | 351/237 |
| 3,415,594 | 12/1968 | Aulhorn | 351/237 |
| 3,655,276 | 4/1972 | Wilkinson | 351/237 |
| 3,945,721 | 3/1976 | Corcoran | 353/84 |
| 3,947,098 | 3/1976 | Paget | 353/103 |
| 5,216,458 | 6/1993 | Andera et al. | 351/243 |

FOREIGN PATENT DOCUMENTS

0954737 4/1964 United Kingdom .................. 351/30

Primary Examiner—William A. Cuchlinski, Jr.
Assistant Examiner—William C. Dowling
Attorney, Agent, or Firm—Dick and Harris

[57] ABSTRACT

A projector slide apparatus for use in a duplex optical chart projector of the type used by optometrists and eye care professionals. The apparatus is insertable into and capable of variable movement within the optical chart projector towards combined simultaneous projection of indicia from an optical acuity chart slide onto a display screen; at different acuity diffusion levels for further testing, evaluating and measuring of the capabilities and sensitivities of the patient's eye.

17 Claims, 2 Drawing Sheets

PROJECTOR SLIDE APPARATUS

BACKGROUND OF THE INVENTION

The present invention relates in general to optical projector slides for use in optical chart projectors used by optometrists and other eye care specialists and, in particular, to a projector slide apparatus for altering the visual contrast background of the symbols or characters located on an optical acuity slide which is being projected through such optical chart projectors onto a display screen towards testing, evaluating and measuring the capabilities of a patient's eye.

For years optometrists and eye care specialists have been utilizing duplex optical chart projectors for analyzing the capabilities of a patient's eyes. Such projectors generally contain areas for insertion of two slides which, when used in combination, simultaneously project through an optical chart projector onto a screen so that a patient can read back to the optometrist what he or she was seeing on the screen. The eye care specialist would then interpret the results towards providing the patient consultation in hopes of diagnosing the patients eye deficiency and therefore bettering the patient's eye sight.

Commonly used within the optical chart projector is a optical acuity slide which contains various symbol and character charts that have different dimensions in not only height and width, but also thickness. Light is transmitted by the optical chart projector through the optical acuity slide so that the symbols or characters are projected onto a display screen. The number of symbols and characters from the optical acuity slide that the patient can read from the screen determines the keenness of the patient's eye sight. Generally speaking, the more of the symbols or characters a patient can read, the better the patient's eye sight may be.

A second slide, known as the horizontal selector slide, is used to test a patient's color perception as well as to isolate various sections of a portion of chart located on the optical acuity slide. A conventional horizontal selector slide has three apertures through which both light and the optical acuity slide may be projected onto the display means. The first aperture in such a horizontal selector slide is a substantially thin, open rectangular aperture which allows the optometrist or eye care specialist to isolate a column or vertical portion of the selected symbols or characters from the optical acuity slide as projected on the display screen. The second aperture is an open aperture utilized to project a full frame of selected portions of the selected symbols or characters of the optical acuity slide onto the display screen.

The final aperture generally found in the horizontal selector slide contains a colorized film, half of which is red and half of which is green, both of which are disposed vertically. The utilization of such film allows for a duochrome test to be performed. The duochrome test permits the optometrist or eye care specialist to test the patient's eyes for color blindness. In contrast to the vertically movable optical acuity slide, such horizontal selector slides are commonly configured for insertion and movement within optical chart projectors in a horizontal manner.

By using the two slides in combination within the optical chart projector, the optometrist or eye care specialist can test many aspects of the human eye. However, these slides do not allow for the testing or measuring of the contrast sensitivity of the patient's eye. Although not widely publicized, the contrast sensitivity of a patient's eye may be clinically significant. Contrast sensitivity testing allows the eye care specialist to detect a cataract, especially incipient cataracts, at earlier stages, as they are forming on the patient's eye. Such contrast sensitivity testing also allows for an earlier determination of when contact lenses are becoming soiled or film-coated. Both cataracts and soiled contact lenses can cause blurred vision and, in more serious cases, may lead to lack of vision.

Currently, such contrast sensitivity testing is only accomplished by providing another set of characters on the optical acuity slide. These characters are "fuzzied" or faded in varying degrees with respect to the normal characters on the optical acuity slide. In order to test contrast sensitivity of the patient, the optometrist or eye care specialist selects the fuzzied or faded characters from the optical acuity slide and projects them onto the display screen which the patient then attempts to read. However, this manner of testing patient's eye does have drawbacks. The incandescent light bulb used in most optical chart projectors does not provide a uniform amount of light to the optical acuity slide. Therefore, the light transmitted through the optical acuity slide onto the display screen may already incorporate a varying degree of contrast. The additional change of contrast embodied by the fuzzied of faded characters on the optical acuity slide has the consequence of causing any measurements taken by the optometrist or eye care specialist to be less precise. Any additional adjustments that may be made in order to compensate for the lack of precision, only makes the procedure more cumbersome and burdensome to both the eye care specialist and the patient. This difficulty in measuring the contrast of the characters as displayed on the screen has prevented the proliferation of such testing within the industry.

It is therefore an object of the present invention to provide a projector slide apparatus that can be utilized in an optical chart projector, in combination with a single optical acuity slide for use in testing the contrast sensitivity of the patient's eye—while offering a greater degree of flexibility in testing acuity diffusion distinctions in all acuity chart portions.

It is additionally an object of the invention to standardize the contrast transmission of the symbols or characters from the optical acuity slide onto the display screen.

Still further an object of the invention, is to incorporate in a single slide the contrast sensitivity testing process as well as the duochrome and other testing processes currently performed on the optical acuity slide as projected onto the display screen.

These and other objects of the invention will become apparent in the light of the present specification and drawings.

SUMMARY OF THE INVENTION

The present invention comprises a projector slide apparatus for use in an integrated duplex optical chart projector for combined projection of a portion of an optical acuity slide upon a display screen, at different contrast diffusion levels.

In the preferred embodiment of the invention, the projector slide apparatus includes a frame having front and back portions and a periphery bounded by at least one edge. Positioned along the frame and extending from the front through to the back are one or more apertures through which light projected by the optical chart projector can pass, so as to appear on the display number simultaneously with selected indicia from the optical acuity slide. One or more diffusion filters are located in the one or more apertures, which filters modify the visual contrast of the background and indicia projected from the optical acuity slide, when the indicia and background are projected onto a display member, simultaneously with the degree of light transmitted through one of the filters onto the same display member. Both the apparatus and the optical acuity slide are individually and independently movable within the optical chart projector so that various selected combinations of indicia and filters may be projected onto the display.

In one preferred embodiment, the selected aperture from within the projector slide apparatus is aligned with the desired indicia from the optical acuity slide, so that a single light beam transmitted by the optical chart projector passes through both the selected aperture of the projector slide apparatus and the desired portion of the optical acuity slide for a combined projection onto the display member. This alignment is facilitated by slide indexing members which are positioned on both the apparatus and the optical acuity slide. The slide indexing members are engaged when the apparatus and optical acuity slide are inserted into the optical chart projector so that the apparatus and optical acuity slide are in the desired position, relative to each other, for the desired combined projection.

The projector slide apparatus frame in one embodiment, is substantially rectangular in shape, having a periphery which consists of a top edge, a bottom edge and two side edges. The apertures are also substantially rectangular in shape and positioned along the length of the frame so that each is respectively centered between the top and bottom edges. Located on either of the top or bottom edges are the slide indexing members utilized in positioning the projector slide apparatus within the optical chart projector. The rectangular configuration of the frame facilitates the horizontal insertion and movement of the projector slide apparatus within the optical chart projector towards simultaneous projection of the medium and/or shape of frame aperture contents onto the display.

The optical acuity slide may also be of rectangular shape, arranged for vertical insertion and movement of the optical acuity slide within the optical chart projector. Alternatively, the optical acuity slide may be circular in shape and capable of rotational movement within the optical chart projector towards simultaneous projection onto the display of both the desired indicia of the optical acuity slide and the desired filter from the present projector slide apparatus.

Preferably, the apparatus contains at least three frame apertures which further contain distinct filters, each of which is of a specific gradation of the visual gray scale for altering the visual contrast of the indicia and background as projected from the optical acuity slide onto the display. The slide indexing members are oriented to correspond to the positions of the filters so that the filter through which the transmission of the indicia will emanate is properly positioned within the optical chart projector. Each such filter in the projector slide apparatus has a different light transmission characteristic, thereby being capable of projecting different levels of contrast as the indicia and background from the optical acuity slide are projected onto the display member.

Additional apertures that do not effect the visual contrast of the indicia, as projected from the optical chart projector, are also positioned along the frame of the projector slide apparatus. A vertical slot permits the projection of only a column or vertical portion of the indicia and background from the optical acuity slide to be transmitted onto the display. A window aperture permits the entirety of the desired indicia and background to be projected onto the display. The last aperture, a color aperture, contains a colorized film, half of which being red and half of which being green. Indicia from the optical acuity slide is projected with the colors from the projector slide apparatus, onto the display member by the optical chart projector, to enable testing of a patient's color perception.

In one embodiment, emanating from each respective side edge of the frame are handles for grasping the apparatus when inserted or moved within the optical chart projector. The handles are positioned so as to avoid inadvertent touching of the front and back of the frame or the apertures contained thereon. Positioned along both the top and bottom edges are the slide indexing members which are comprised of notches extending past the respective top and bottom edge, down into the respective front or back of the frame.

In yet another embodiment, the projector slide apparatus includes a frame which is circular in shape and which contains one or more square apertures. The slide indexing members corresponding to the respective apertures are positioned along the peripheral side edge of the circular frame so that the beam of light transmitted by the optical chart projector through the present slide apparatus also penetrates the aligned optical acuity slide, for projecting the indicia and background onto the display member. The optical acuity slide of this embodiment is also circular in configuration, with the optical acuity slide and corresponding indicia and background being arranged for rotational movement within the optical chart projector.

Preferably, three of the one or more apertures within this circular frame contain three distinct filters, each capable of altering the visual contrast of the indicia and background as projected through the respective filter and onto the display member so that no two filters perceivably alter the visual contrast in the identical manner. Additional apertures within this frame do not effect the visual contrast of the indicia as projected from the optical chart projector. The vertical slot permits the projection of only a column or vertical portion of the indicia and background from the optical acuity slide to be transmitted onto the display. Similarly, the horizontal slot permits only a row or horizontal portion of the indicia and background to be transmitted onto the display. A window aperture permits the entirety of the desired indicia and background to be projected onto the display. The color aperture contains a colorized film, half of which being red and half of which being green. When indicia from the optical acuity slide and the colors are simultaneously projected onto the display by the optical chart projector, the patient's color perception may be tested.

In an alternative embodiment, the optical acuity slide is penetrated by a beam of light towards projecting the indicia and background from the optical acuity slide onto the display. A second beam of light passes through one of the apertures, and thereby one of the filters, located on the projector slide apparatus and simultaneous projected onto the same display. Both the optical acuity slide and the projector slide apparatus contain slide indexing members so as to facilitate the positioning of each within the optical chart projector during such simultaneous projection. In this manner the visual contrast of the indicia and background as perceived by the patient's eye from the display is again altered for analysis.

DETAILED DESCRIPTION OF THE DRAWINGS

While this invention is susceptible of embodiment in many different forms, there is shown in the drawings and will herein be described in detail, several specific embodiments, with the understanding that the present disclosure is to be considered as an exemplification of the principles of the invention and is not intended to limit the embodiments illustrated.

Figure 1:
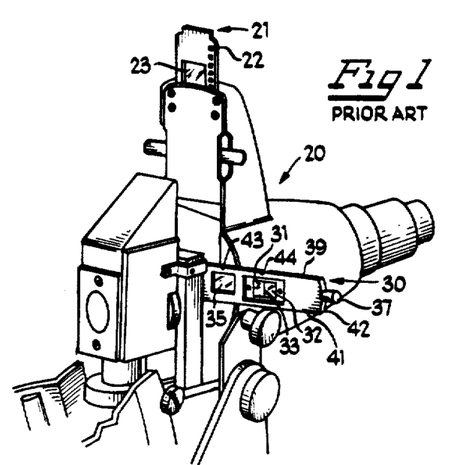
FIG. 1 of the drawings is a side perspective view of a prior art optical acuity chart slide means and prior art horizontal selector slide, as inserted and utilized in combination within an optical chart projector.
Figures 6, 7, 8, 11, 12:
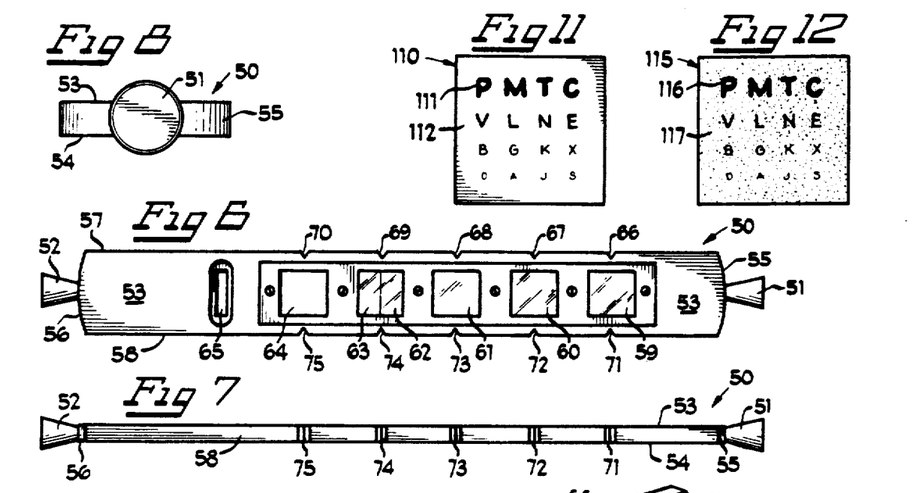
FIG. 6 is an elevational front view of the projector slide apparatus of FIG. 5 wherein the apertures are positioned longitudinally along the front face, through to the back face of the invention.
FIG. 7 is a top plan view of the projector slide apparatus of FIG. 6, demonstrating the indexing notches for proper location of the projector slide apparatus within the optical chart projector.
FIG. 8 is an elevated side view of the projector slide apparatus of FIG. 6 showing a handle attached to the side edge.
FIG. 11 of the drawings is an elevated front view of the indicia and background as projected onto the display means by the optical chart projector, without any modification of the visual contrast transmission thereof.
FIG. 12 is an elevated front view of the indicia and background as projected by the optical chart projector onto the display means, with alteration of the visual contrast transmission of the background as affected by the present invention.

Integrated duplex optical chart projector 20 is shown in FIG. 1 with optical acuity chart slide means 21 vertically inserted into the optical chart projector 20 while prior art projector slide 30 is horizontally inserted into optical chart projector 20, for horizontal movement therewithin. By engaging slide indexing means 22 of optical acuity chart slide means 21, within optical chart projector 20, selected portions of indicia 23 can be projected from optical chart projector 20 onto a display means. When prior art projector slide 30 is inserted into optical chart projector 20, light emanating from optical chart projector 20 is simultaneously transmitted through both optical acuity chart slide means 21 and prior art projector slide 30. Such simultaneous projection enables portions of indicia 23 from acuity chart slide means 21 to be affected by the prior art features of the projector slide 30; without changing the contrast of the transmission of such indicia onto display means such as screen 110 (FIG. 11). By utilizing handle 37 on edge 42 of projector slide 30, the operator of optical chart projector 20 is able to horizontally insert and move prior art projector slide 30 in optical chart projector 20, through engaging respective slide indexing means 43 and 44.

Figures 2, 3, 4:
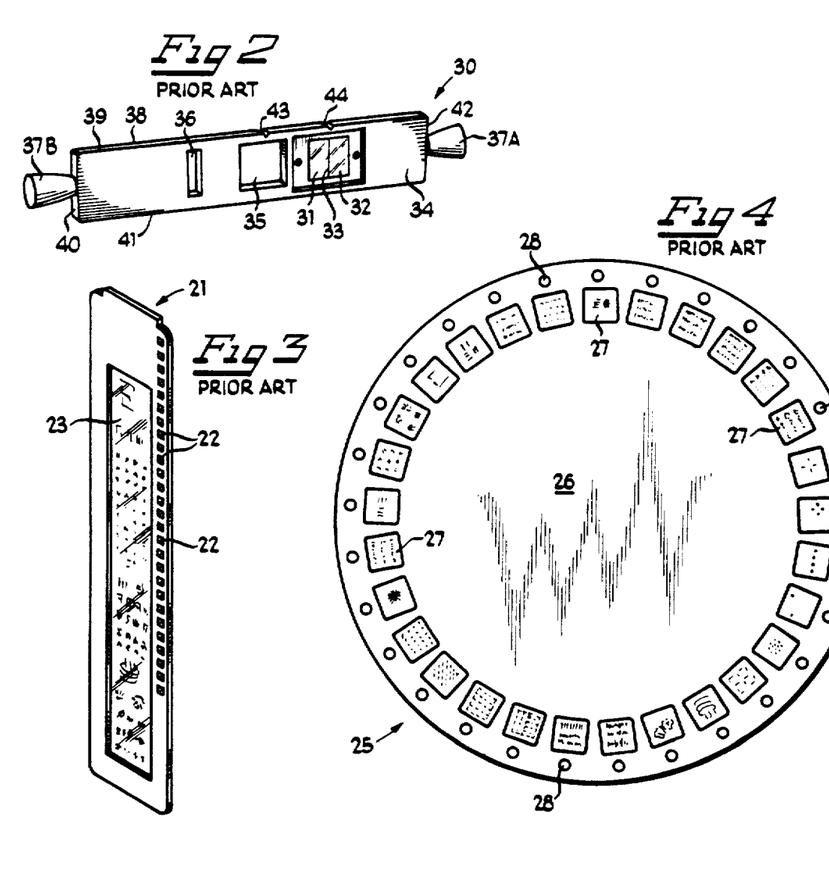
FIG. 2 of the drawings is a side perspective view of prior art horizontal selector slide in a rectangular configuration, having three transmission apertures along its longitudinal axis.
FIG. 3 is a front perspective view of a conventional optical acuity chart slide means, in a substantially rectangular configuration for vertical insertion and reciprocation within the optical chart projector.
FIG. 4 is an elevated front view of conventional optical acuity chart slide means in a circular configuration, for rotational movement within the optical chart projector, for projection of selected indicia.

As further illustrated in FIG. 2, prior art slide 30 is in a substantially rectangular configuration. Handles 37a and 37b, operably and respectively attached to side edges 42 and 40, are utilized by the operator to horizontally insert and move prior art projector slide 30 in optical chart projector 20. When inserted, the prior art projector slide 30 restricts the complete projection of indicia 23 from optical acuity chart slide means 21 through optical chart projector 20 and onto display means by projecting indicia 23 through one of respective apertures 36, 35 and/or 31-32. Vertical slotted aperture 36 allows only a column or vertical portion of selected indicia 23 on optical acuity chart 21 to be projected through optical acuity chart projector 20 onto display means. Similarly, clear aperture 35 permits the entirety of selected indicia portion 23 to be projected onto the display means. Color perception aperture 31-32 is utilized to further restrict the color perception of the patient's eye when viewing indicia 23 as projected through optical chart projector 20. Color perception aperture 31-32 contains a bi-color film which is bisected along the latitudinal axis 33 of aperture 31-32. First portion 31 comprises a green colored film while second portion 32 comprises a red colored film. As prior art projector slide 30 is inserted into optical chart projector 20 so that slide indexing means 44 is operably engaged therewithin, securing the prior art projector slide 30 in a proper position within the optical chart projector 20, the operator is able to simultaneously project not the only indicia 23 of optical acuity chart 21, but also the color perception aperture 31-32—through the lens of optical chart projector 20 and onto display means, such as a projection screen, towards analyzing and measuring the color perception of the patient's eyes.

FIG. 3 is a front perspective view of prior art optical acuity chart slide means 21 in a substantially rectangular configuration having slide indexing means 22 along one of its side edges. Indicia 23 are operably positioned in charts or regions capable of being projected through optical chart projector 20 when respective ones of slide indexing means 22 are engaged and utilized within the optical chart projector 20. Optical acuity chart slide means 25 of FIG. 4 is in a substantially circular configuration. In this circular configuration, indicia charts or regions 27 are operably positioned about the circumference of the acuity chart 25, so that upon rotation of optical acuity chart slide means 25 within optical chart projector 20, different and selected portions of indicia 27 may be displayed through optical chart projector 20 onto display means. Slide indexing means 28 are also operably positioned about the periphery of the optical acuity chart slide means so as to correspond to the respective position of indicia 27. When engaged, slide indexing means 28 ensure the stability and positioning of optical acuity chart slide means within optical chart projector 20 so that solely the respective and desired indicia portion 27 is projected from optical acuity chart projector 20.

Figure 5:
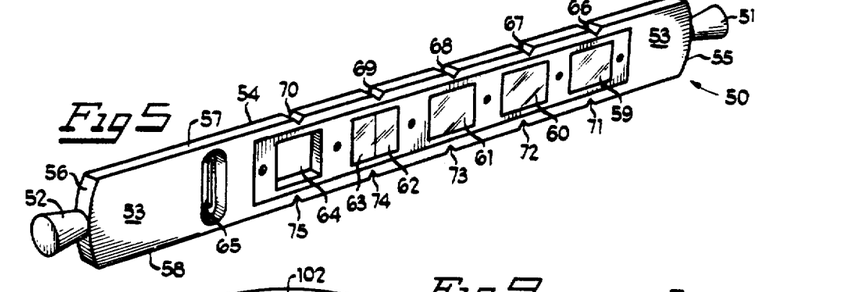
FIG. 5 is a side perspective view of the projector slide apparatus corresponding to the present invention, having six apertures in which at least three apertures contain diffusion filter means capable of modifying the visual contrast transmission of selected indicia of optical acuity chart slide means, as perceived by a patient's eye.

FIG. 5 shows projector slide apparatus 50 of the present invention in a rectangular configuration having front face 53, a back face 54, top edge 57, bottom edge 58 and side edges 55 and 56. Apertures 59, 60, 61, 62-63, 64 and 65 emanate from front face 53 through projector slide apparatus 50 to back face 54 thereby permitting the transmission of light therethrough. Apertures 59, 60 and 61 contain diffusion filter means for altering the visual contrast of the indicia from the optical acuity chart slide means 21 when light is simultaneously transmitted through both projector slide apparatus 50 and optical acuity slide means 29 simultaneously by the optical chart projector 20, for projection onto display means 110. Ideally, diffusion filter means of apertures 59, 60 and 61 will be of three distinct gradation, varying along the visual gray scale, so that the visual contrast of the indicia and background projected by optical chart projector is distinctly displayed.

Color perception aperture 62-63 contains color film portions through which the indicia of the associated optical acuity chart may be projected. The first portion 63 of the color perception aperture 62-63 is of a green color while the second portion 62 is of a red color. Clear aperture 64 is utilized in combination with the optical acuity chart so as to display the entirety of a selected portion of the optical acuity chart on display means without altering or modifying the contrast transmission of such indicia by optical chart projector. Similarly, vertical slotted aperture 65 may be utilized to project a column or vertical portion of the selected indicia through the projector onto display means without altering the contrast transmission of the indicia. In order to ensure proper positioning of respective apertures 59, 60, 61, 62-63, 64 and 65 within optical chart projector, indexing notches 66 through 75 are operably positioned along both top edge 57 and bottom edge 58 of projector slide apparatus 50.

Indexing notches 71-75 are shown along bottom edge 58 in FIG. 7 corresponding to the distance within the optical chart projector that the projector slide apparatus 50 must be moved for projection through one of desired apertures 59, 60, 61, 62-63, 64 and 65. For instance, to utilize aperture 59 and diffusion filter therewithin, projector slide apparatus 50 would be inserted into optical chart projector so as to engage indexing notches 66 and 71 respectively, thereby positioning projector slide apparatus 50, for alignment with selected portions of the optical acuity chart slide means, for projection, in turn, onto the display means.

Also shown in FIG. 7 are handles 51 and 52 which are attached to side edges 55 and 56 respectively of projector slide apparatus 50. Handles 51 and 52 are utilized by the operator of the optical chart projector, so as to limit the need for handling or inadvertently touching the front and back faces 53 and 54 or apertures 59, 60, 61, 62-63, 64, and 65 of the projector slide apparatus 50 when inserted into the optical chart projector. As shown in FIG. 8, handle 51 protrudes from side edge 55 and has a diameter greater than the width of side edge 55 thereby protruding past front and back faces 53 and 54 of projector slide apparatus 50.

Figure 9:
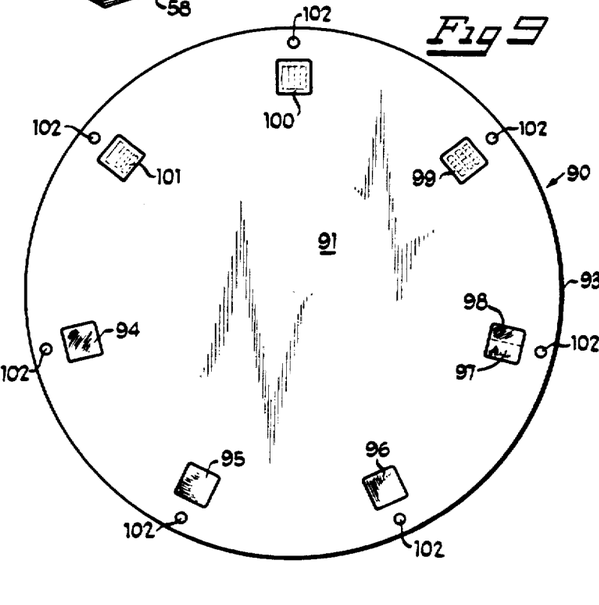
FIG. 9 of the drawings is an elevated front view of the projector slide apparatus of the present invention in a circular configuration, having seven apertures located about its periphery.
Figure 10:
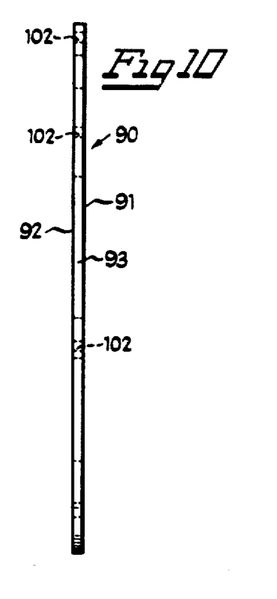
FIG. 10 is a side view of the projector slide apparatus of FIG. 9 showing the slide indexing means along both the front and back faces, along the top and bottom edges.

Projector slide apparatus 90 is shown in a substantially circular embodiment in FIG. 9. Apertures 94, 95, 96, 97-98, 99, 100 and 101 are positioned about projector slide apparatus 90, adjacent to peripheral side edge 93. Apertures 94, 95 and 96 contain diffusion filter means each of which contain different light transmission characteristics thereby causing different visual acuity contrast when indicia from optical acuity chart slide means are projected through the respective filters from optical chart projector and onto display means 115. Color perception aperture 97-98 has green color film portion 97 and red color film portion 98 to enable testing a patient's eye for color perception when used in combination with optical acuity chart slide means. Clear aperture 99 allows for the entirety of selected portions of indicia to be transmitted through optical chart projector onto display means when used in combination with the optical acuity chart slide means. Similarly, vertical slotted aperture 100 allows for only a column or vertical portion of the selected segment of indicia to be displayed upon display means. Horizontal slotted aperture 101 further provides only a row or a horizontal portion of indicia from selected portions of the optical acuity chart slide means to be projected onto display means by optical chart projector. When utilizing apertures 99, 100 and 101 respectively, the projected indicia from the optical acuity chart slide means is projected onto the display means with no alteration or modification of the visual contrast transmitted that would be perceived by the patient's eye. Slide indexing means 102 ensure that solely the desired aperture 94, 95, 96, 97-98, 99, 100 and 101 that are used to project the indicia of optical acuity chart slide means, are positioned adjacent to respective ones of apertures 94, 95, 96, 97-98, 99, 100 and 101 and proximate to side edge 93, as shown in FIG. 10.

FIGS. 11 and 12 show display means 110 and 115, respectively, as projection screens receiving images as projected by an optical chart projector such a projector 20. In FIG. 11, indicia 111 are projected in a clear manner with no change in the visual contrast of background 112 on display means 110. FIG. 12 demonstrates indicia 116 having an altered visual contrast acuity due to the contrast transmission of background 117 onto display means 115.

The foregoing description and drawings merely explain and illustrate the invention and the invention is not limited thereto except in so far as the appended claims are so limited, that those skilled in the art who have the disclosure before them will be able to make modifications and variations therein without departing form the scope of the invention.

What is claimed is:

1. A projector slide apparatus for use in association with an integrated, duplex optical chart projector, said slide apparatus being operably positionable for combined projection with optical acuity chart slide means simultaneously, to project and display at least a selected portion of said optical acuity chart slide means having projectable indicia and background described thereupon, at different acuity diffusion levels on display means, for the testing, evaluation and measurement of the capabilities and sensitivities of a patient's eye, said projector slide apparatus comprising:

> frame means having a front face and a back face positioned opposite to said front face, each of said front and back faces traversing substantially the same longitudinal and latitudinal axes, each of said front and back faces having at least one or more side edges operably positioned about their respective periphery between said front and back faces of said frame means;
>
> one or more apertures operably positioned in said front face and extending through said frame means to said back face so as to permit light to be transmitted through at least one of said one or more apertures towards and onto said display means, simultaneously with said selected portion of said optical acuity chart slide means when said projector slide apparatus and said optical acuity chart slide means are operably engaged in said optical chart projector; and
>
> one or more acuity diffusion filter means operably positioned within selected ones of said one or more apertures, at least one of said one or more acuity diffusion filter means describing a fixed, nonadjustable contrast gradation for operable alignment with selected portions of said optical acuity chart slide means,
>
> said one or more acuity diffusion filter means being capable of modifying the visual contrast between said projectable indicia and said background of said portion of displayed optical acuity chart slide means when simultaneously projected upon said display means by said integrated, duplex optical chart projector,
>
> each of said one or more acuity diffusion filter means and said selected portion of said acuity chart slide means having said desired projectable indicia and background associated therewith, being independently variable in position within said optical chart projector, respectively, to enable combinations of selected portions of each as desired by a user.

2. The projector slide apparatus according to claim 1 wherein:

> said one or more apertures in said frame means are operably alignable with said selected portion of said acuity chart slide means to enable a single beam of light projected by said integrated, duplex optical chart projector to be simultaneously transmitted through both said selected one of said apertures, containing said selected acuity diffusion filter means and said selected portion of said optical acuity chart slide means, and in turn, said selected indicia and background portion described thereon, for operable, combined visual projection onto said display means;
>
> each of said projector slide apparatus and said acuity chart slide means having slide indexing means operably and respectively associated therewith so as to facilitate the proper positioning of each relative to the other to effectively ensure the operable alignment of the selected portions of each together with said simultaneously transmitted single beam of light through each, for said simultaneous combined projection onto said display means.

3. The projector slide apparatus according to claim 2 wherein:

> said projector slide apparatus is positioned for horizontal variable movement within said optical chart projector along said longitudinal axis of said projector slide apparatus towards combined, simultaneous projection of said selected portions of said optical acuity chart slide means and said projector slide apparatus onto said display means.

4. A projector slide apparatus for use in association with an integrated, duplex optical chart projector, said slide apparatus being operably positionable for combined projection with optical acuity chart slide means simultaneously, to project and display at least a selected portion of said optical acuity chart slide means having projectable indicia and background described thereupon, at different acuity diffusion levels on display means, for the testing, evaluation and measurement of the capabilities and sensitivities of a patient's eye, said projector slide apparatus comprising:

> frame means having a front face and a back face positioned opposite to said front face, each of said front and back faces traversing substantially the same longitudinal and latitudinal axes, each of said front and back faces having at least one or more side edges operably positioned about their respective periphery between said front and back faces of said frame means;
>
> one or more apertures operably positioned in said front face and extending through said frame means to said back face so as to permit light to be transmitted through at least one of said one or more apertures towards and onto said display means, simultaneously with said selected portion of said optical acuity chart slide means when said projector slide apparatus and said optical acuity chart slide means are operably engaged in said optical chart projector; and
>
> one or more acuity diffusion filter means operably positioned within selected ones of said one or more apertures,
>
> said one or more acuity diffusion filter means being capable of modifying the visual contrast between said projectable indicia and said background of said portion of displayed optical acuity chart slide means when simultaneously projected upon said display means by said integrated, duplex optical chart projector;
>
> each of said one or more acuity diffusion filter means and said selected portion of said acuity chart slide means having said desired projectable indicia and background associated therewith, being independently variable in position within said optical chart projector, respectively, to enable combinations of selected portions of each as desired by a user,
>
> said one or more apertures in said frame means being operably alignable with said selected portion of said acuity chart slide means to enable a single beam of light projected by said integrated, duplex optical chart projector to be simultaneously transmitted through both said selected one of said apertures, containing said selected acuity diffusion filter means and said selected portion of said optical acuity chart slide means, and in turn, said selected indicia and background portion described thereon, for operable, combined visual projection onto said display means, each of said projector slide apparatus and said acuity chart slide means having slide indexing means operably and respectively associated therewith so as to facilitate the proper positioning of each relative to the other to effectively ensure the operable alignment of the selected portion of each other with said simultaneously transmitted single beam of light through each, for said simultaneous combined projection onto said display means;

said frame means being substantially rectangular in shape and operably insertable into said optical chart projector for said independent variable positioning therewithin;

said one or more side edges of said frame means consisting of a top edge, a bottom edge operably positioned opposite to said top edge, and tow side edges operably positioned opposite to each other;

each of said one or more apertures in said frame means being substantially rectangular in shape and operably positioned between said front and back faces so as to be positioned between and substantially equidistant from said top and bottom edges, with said one or more apertures being substantially bisected by said longitudinal axis along said front and back faces; and said slide indexing means being operably positioned along at least one of said top and bottom edges, towards properly positioning said frame means when engaged in said optical projector, for the simultaneous transmission of said single beam of light through said projector slide apparatus and said optical acuity chart slide means.

5. The projector slide apparatus according to claim 4 wherein:

said optical acuity chart slide means is substantially rectangular in shape and operably insertable into said optical chart projector for said independent variable positioning therewithin.

6. The projector slide apparatus according to claim 5 wherein:

said optical acuity chart slide means is positioned for vertical variable movement within said optical chart projector towards combined, simultaneous projection of selected portions of said optical acuity chart slide means and said selected portions of said projector slide apparatus onto said display means.

7. The projector slide apparatus according to claim 4 wherein:

said optical acuity chart slide means is substantially circular in shape, said optical acuity chart slide means being capable of rotational movement within said optical chart projector towards combined, simultaneous projection of said selected portions of said optical acuity chart slide means and said selected portions of said projector slide apparatus onto said display means.

8. The projector slide apparatus according to claim 4 in which each of said one or more acuity diffusion filter means comprises a light transmission filter having a particular gradation of the visual gray scale over the entirety of each said filter respectively;

each of said one or more slide indexing means serving to operably position a selected one of said one or more acuity diffusion filter means within said frame means when operably engaged within said optical projector so as to measurably alter the visual contrast acuity of said indicia and background of said selected portion of said optical acuity chart slide means, for perception by said patient's eye during projection upon said display means.

9. The projector slide apparatus according to claim 8 wherein:

said one or more acuity diffusion filter means comprises at least three distinct acuity diffusion filters operably positioned within at least three respective ones of said one or more apertures in said frame means;

each of said at least three acuity diffusion filter means having one of at least three different light transmission characteristics so as to collectively provide at least three distinct levels for altering the visual contrast acuity of said optical acuity chart slide means, as projected by said optical chart projector onto said display means, each of said at least three acuity diffusion filters altering the optical gradient of light transmission along said visual gray scale.

10. The invention according to claim 9 wherein said projector slide apparatus further comprises:

a vertically slotted aperture for the clear transmission of a column of said selected portion of said optical acuity chart slide means to be projected upon said display means by said optical chart projector without any alteration of the visual contrast of said transmitted, selected indicia and background of said optical acuity chart slide means onto said display means;

a clear aperture for transmission of the entirety of said selected portion of said optical acuity chart slide means to be projected upon said display means by said optical chart projector without any alteration of the visual contrast of said transmitted, selected indicia and background of said optical acuity chart slide means onto said display means;

a color perception aperture having positioned therewithin color film means towards analyzing color perception by said patient's eye;

said color film means consisting of a first red portion and a second green portion, each of which first red and second green portions covering at least a portion of said aperture, towards combined projection with said optical acuity chart through said optical chart projector towards said determination of color perception by said patient's eye.

11. The projector slide apparatus according to claim 10 in which:

said one or more slide indexing means comprises a plurality of notches operably positioned at said top and bottom edges of said frame means so as to position said frame means to a location within said optical chart projector towards the utilization of any one of said apertures, when projecting said selected portion of said optical acuity chart slid through said optical chart projector onto said display means.

12. The invention according to claim 4 in which said projector slide apparatus further includes one or more handles for inserting and positioning said projector slide apparatus within said optical slide projector, said handles being operably attached to opposite ones of said two side edges of said frame means, respectively.

13. A projector slide apparatus for use in association with an integrated, duplex optical chart projector, said slide apparatus being operably positionable for combined projection with optical acuity chart slide means simultaneously, to project and display at least a selected portion of said optical acuity chart slide means having projectable indicia and background described thereupon, at different acuity diffusion levels on display means, for the testing, evaluation and measurement of the capabilities and sensitivities of a patient's eye, said projector slide apparatus comprising:

frame means having a front face and a back face positioned opposite to said front face, each of said front and back faces traversing substantially the same longitudinal and latitudinal axes, each of said front and back faces having at least one or more side edges operably positioned about their respective periphery between said front and back faces of said frame means;

one or more apertures operably positioned in said front face and extending through said frame means to said back face so as to permit light to be transmitted through at least one of said one or more apertures towards and onto said display means, simultaneously with said selected portion of said optical acuity chart slide means when said projector slide apparatus and said optical acuity chart slide means are operably engaged in said optical chart projector; and one or more acuity diffusion filter means operably positioned within selected ones of said one or more apertures, said one or more acuity diffusion filter means being capable of modifying the visual contrast between said projectable indicia and said background of said portion of displayed optical acuity chart slide means when simultaneously projected upon said display means by said integrated, duplex optical chart projector;

each of said one or more acuity diffusion filter means and said selected portion of said acuity chart slide means having said desired projectable indicia and background associated therewith, being independently variable in position within said optical chart projector, respectively, to enable combinations of selected portions of each as desired by a user, said one or more apertures in said frame means being operably alignable with said selected portion of said acuity chart slide means to enable a single beam of light projected by said integrated, duplex optical chart projector to be simultaneously transmitted through both said selected one of said apertures, containing said selected acuity diffusion filter means and said selected portion of said optical acuity chart slide means, and in turn, said selected indicia and background portion described thereon, for operable, combined visual projection onto said display means, each of said projector slide apparatus and said acuity chart slide means having slide indexing means operably and respectively associated therewith so as to facilitate the proper positioning of each relative to the other to effectively ensure the operable alignment of the selected portion of each together with said simultaneously transmitted single beam of light through each, for said simultaneous combined projection onto said display means;

said frame means being substantially circular in shape;

said one or more apertures being substantially rectangular in shape and operably positioned through said front and back faces; and said one or more slide indexing means being operably positioned adjacent the peripheral edge of said circular frame means towards operably positioning said frame means when engaged in said optical projector, for the simultaneous transmission of light through both said projector slide apparatus and said optical acuity chart slide means, for combined projection upon said display means.

14. The projector slide apparatus according to claim 13 wherein:

said optical acuity chart slide means is substantially circular in shape;

said optical acuity chart slide means being capable of rotational movement within said optical chart projector towards combined, simultaneous projection of selected portions of both said optical acuity chart slide means and said selected portions of said projector slide apparatus, onto said display means.

15. The projector slide apparatus according to claim 13 in which:

said one or more acuity diffusion filter means comprises at least three distinct acuity diffusion filters operably positioned within at least three respective ones of said one or more apertures in said frame means;

each of said at least three acuity diffusion filter means having one of at least three different light transmission characteristics so as to collectively provide at least three distinct levels for altering the visual contrast acuity of said optical acuity chart slide means, as projected by said optical chart projector onto said display means, each of said at least three acuity diffusion filters altering the optical gradient of light transmission along the visual gray scale;

a vertically slotted aperture for the clear transmission of a column of said selected portion of said optical acuity chart slide means to be projected upon said display means by said optical chart projector without any alteration of the visual contrast of said transmitted, selected indicia and background of said optical acuity chart slide means onto said display means;

a horizontally slotted aperture for clear transmission of a row of said selected portion of said optical acuity chart slide means to be projected upon said display means by said optical chart projector without any alteration of the visual contrast of said transmitted, selected indicia and background of said optical acuity chart slide means onto said display means;

a clear apertures for transmission of the entirety of said selected portion of said optical acuity chart slide means to be projected upon said display means by said optical chart projector without any alteration of said transmission of said selected indicia and background of said optical acuity chart slide means onto said display means;

a color perception aperture having positioned therewithin color film means towards analyzing color perception by said patient's eye;

said color film means consisting of a first red portion and a second green portion, each of which first and second portions covering at least a portion of said aperture towards combined projection with said optical acuity chart through said optical chart projector towards said determination of color perception by said patient's eye.

16. A projector slide apparatus for use in association with an integrated, duplex optical chart projector, said slide apparatus being operably positionable for combined projection with optical acuity chart slide means simultaneously, to project and display at least a selected portion of said optical acuity chart slide means having projectable indicia and background described thereupon, at different acuity diffusion levels on display means, for the testing, evaluation and measurement of the capabilities and sensitivities of a patient's eye, said projector slide apparatus comprising:

frame means having a front face and a back face positioned opposite to said front face, each of said front and back faces traversing substantially the same longitudinal and latitudinal axes, each of said front and back faces having at least one or more side edges operably positioned about their respective periphery between said front and back faces of said frame means;

one or more apertures operably positioned in said front face and extending through said frame means to said back face so as to permit light to be transmitted through at least one of said one or more apertures towards and onto said display means, simultaneously with said selected portion of said optical acuity chart slide means when said projector slide apparatus and said optical acuity chart slide means are operably engaged in said optical chart projector; and one or more acuity diffusion filter means operably positioned within selected ones of said one or more apertures, said one or more acuity diffusion filter means being capable of modifying the visual contrast between said projectable indicia and said background of said portion of displayed optical acuity chart slide means when simultaneously projected upon said display means by said integrated, duplex optical chart projector;

each of said one or more acuity diffusion filter means and said selected portion of said acuity chart slide means having said desired projectable indicia and background associated therewith, being independently variable in position within said optical chart projector, respectively, to enable combinations of selected portions of each as desired by a user, said one or more apertures in said frame means being illuminated by a first beam of light emanating from said integrated, duplex optical chart projector through said selected one of said one or more apertures, and in turn, said selected acuity diffusion filer means for projection upon said display means, said selected portion of said optical acuity chart slide means being illuminated by a second beam of light emanating from said integrated, duplex optical chart projector through said selected portion of said optical acuity chart slide means, and in turn, said selected indicia and background portion described thereon, for projection upon said display means, each of said projector slide apparatus and said acuity chart slide means having slide indexing means operably and respectively associated therewith so as to facilitate the proper positioning of each relative to the projection of the other to effectively ensure the operable alignment of the selected portions of said projector slide apparatus and said optical acuity chart slide during said simultaneous projection onto said display means.

17. The projector slide apparatus according to claim 1 in which said display means comprises a screen.

* * * * *

UNITED STATES PATENT AND TRADEMARK OFFICE
CERTIFICATE OF CORRECTION

PATENT NO. : 5,302,982  
DATED : April 12, 1994  
INVENTOR(S) : Deanne I. Davis

It is certified that error appears in the above-indentified patent and that said Letters Patent is hereby corrected as shown below:

| | |
|---|---|
| Col. 11, Line 8 | After "portion" insert -- s --. |
| Col. 11, Line 18 | After "and" delete "tow" and insert -- two --. |
| Col. 12, Line 56 | Delete "any" and insert -- only --. |
| Col. 12, Line 57 | Delete "slid" and insert -- slide --. |
| Col. 13, Line 36 | After "projector" delete ";" and insert -- , --. |
| Col. 13, Line 61 | After "portion" insert -- s --. |
| Col. 14, Line 52 | After "clear" delete "apertures" and insert -- aperture --. |

UNITED STATES PATENT AND TRADEMARK OFFICE
CERTIFICATE OF CORRECTION

PATENT NO. : 5,302,982
DATED : April 12, 1994
INVENTOR(S) : Deanne I. Davis

It is certified that error appears in the above-indentified patent and that said Letters Patent is hereby corrected as shown below:

Column 16, line 15, after "diffusion" delete "filer and insert —filter—.

Signed and Sealed this

Sixteenth Day of May, 1995

Attest:

BRUCE LEHMAN

Attesting Officer

Commissioner of Patents and Trademarks